(12) United States Patent
Geissler

(10) Patent No.: US 8,652,142 B2
(45) Date of Patent: Feb. 18, 2014

(54) OSTEOTOMY SYSTEMS

(75) Inventor: William B. Geissler, Brandon, MS (US)

(73) Assignee: Acumed LLC, Hillsboro, OR (US)

( * ) Notice: Subject to any disclaimer, the term of this patent is extended or adjusted under 35 U.S.C. 154(b) by 1075 days.

(21) Appl. No.: 11/413,631

(22) Filed: Apr. 28, 2006

(65) Prior Publication Data

US 2007/0270850 A1 Nov. 22, 2007

(51) Int. Cl.
*A61F 5/00* (2006.01)

(52) U.S. Cl.
USPC .......................................................... 606/87

(58) Field of Classification Search
USPC ............. 606/57, 71, 87, 79, 84, 280–299, 88, 606/90, 105
See application file for complete search history.

(56) References Cited

U.S. PATENT DOCUMENTS

| | | | |
|---|---|---|---|
| 3,244,170 A | 4/1966 | McElvenny | |
| 3,386,437 A | 6/1968 | Treace | |
| 3,604,414 A | 9/1971 | Borges | |
| 3,763,855 A | 10/1973 | McAtee | |
| 4,119,092 A | 10/1978 | Gil | |
| 4,750,481 A | 6/1988 | Reese | |
| 4,913,137 A | 4/1990 | Azer et al. | |
| 4,929,247 A * | 5/1990 | Rayhack | 606/53 |
| 5,021,056 A | 6/1991 | Hofmann et al. | |
| 5,042,983 A | 8/1991 | Rayhack | |
| 5,108,398 A | 4/1992 | McQueen et al. | |
| 5,122,146 A | 6/1992 | Chapman et al. | |
| 5,176,685 A * | 1/1993 | Rayhack | 606/87 |
| 5,254,119 A | 10/1993 | Schreiber | |
| 5,281,224 A | 1/1994 | Faccioli et al. | |
| 5,352,228 A | 10/1994 | Kummer et al. | |
| 5,413,579 A | 5/1995 | Tom Du Toit | |
| 5,549,609 A | 8/1996 | Frankel et al. | |
| 5,665,086 A | 9/1997 | Itoman et al. | |
| 5,722,978 A * | 3/1998 | Jenkins, Jr. | 606/87 |
| 5,766,174 A | 6/1998 | Perry | |
| 5,935,128 A * | 8/1999 | Carter et al. | 606/86 B |
| 5,951,557 A | 9/1999 | Luter | |
| 5,976,138 A | 11/1999 | Baumgart et al. | |
| 6,007,535 A * | 12/1999 | Rayhack et al. | 606/57 |
| 6,027,504 A * | 2/2000 | McGuire | 606/87 |
| 6,159,213 A | 12/2000 | Rogozinski | |
| 6,200,317 B1 | 3/2001 | Aalsma et al. | |
| 6,206,882 B1 | 3/2001 | Cohen | |
| 6,287,307 B1 | 9/2001 | Abboudi | |
| 6,689,139 B2 * | 2/2004 | Horn | 606/87 |
| 7,090,676 B2 | 8/2006 | Huebner et al. | |

(Continued)

FOREIGN PATENT DOCUMENTS

| | | |
|---|---|---|
| DE | 1248228 | 8/1967 |
| EP | 0415837 | 8/1990 |

(Continued)

OTHER PUBLICATIONS

Rayhack Osteotomy Systems, Ulnar Shortening Surgical Technique Manual, May 1, 2000.

(Continued)

*Primary Examiner* — Eduardo C Robert
*Assistant Examiner* — Atiya Mahmud
(74) *Attorney, Agent, or Firm* — Kolisch Hartwell, P.C.

(57) ABSTRACT

Systems, including methods, apparatus, and kits, for performing osteotomies to cut bone and, optionally, to adjust bone length.

18 Claims, 4 Drawing Sheets

(56) References Cited

U.S. PATENT DOCUMENTS

| | | |
|---|---|---|
| 7,153,309 B2 | 12/2006 | Huebner et al. |
| 7,189,237 B2 | 3/2007 | Huebner |
| 7,326,212 B2 | 2/2008 | Huebner |
| 2002/0183757 A1* | 12/2002 | Michelson ............ 606/71 |
| 2004/0102775 A1 | 5/2004 | Huebner |
| 2004/0102778 A1 | 5/2004 | Huebner et al. |
| 2004/0106926 A1* | 6/2004 | Leitner et al. ............ 606/87 |
| 2004/0116930 A1 | 6/2004 | O'Driscoll et al. |
| 2004/0122429 A1 | 6/2004 | Phillips et al. |
| 2004/0260291 A1 | 12/2004 | Jensen |
| 2005/0065522 A1* | 3/2005 | Orbay ............ 606/69 |
| 2005/0085818 A1 | 4/2005 | Huebner |
| 2005/0154392 A1* | 7/2005 | Medoff et al. ............ 606/69 |
| 2005/0192578 A1 | 9/2005 | Horst et al. |
| 2005/0234458 A1 | 10/2005 | Huebner |
| 2005/0240187 A1 | 10/2005 | Huebner et al. |
| 2005/0267484 A1* | 12/2005 | Menzner ............ 606/87 |
| 2005/0277941 A1* | 12/2005 | Trumble et al. ............ 606/79 |
| 2007/0173840 A1 | 7/2007 | Huebner |
| 2007/0185493 A1 | 8/2007 | Feibel et al. |

FOREIGN PATENT DOCUMENTS

| | | |
|---|---|---|
| FR | 2720623 A1 | 12/1995 |
| GB | 2 451 401 A | 1/2009 |
| JP | H10-137253 | 5/1998 |
| SU | 1637774 | 3/1991 |
| SU | 1644938 | 4/1991 |
| WO | 8906948 | 8/1989 |
| WO | 2007127994 A2 | 11/2007 |

OTHER PUBLICATIONS

Philogene, Pedro, Authorized officer of the International Searching Authority, International Search Report, International Application No. PCT/US07/67829, search date: Mar. 29, 2008.

European Patent Office, European (pending counterpart) Application Serial No. EP07782942; search completed: Apr. 17, 2012; mail date: Apr. 24, 2012.

Japan Patent Office, Notice of Reasons for Rejection, counterpart application, Application Serial No. 2009-508012; Notice mailed Jan. 31, 2012.

European Patent Office, "Communication Pursuant to 94(3) EPC" in connection with related European Patent Application No. 07782942.2, dated Jan. 25, 2013, 4 pages.

Notice of Reasons for Rejection in connection with corresponding Japanese Patent Application No. 2009-508012, Oct. 30, 2012, 4 pages.

* cited by examiner

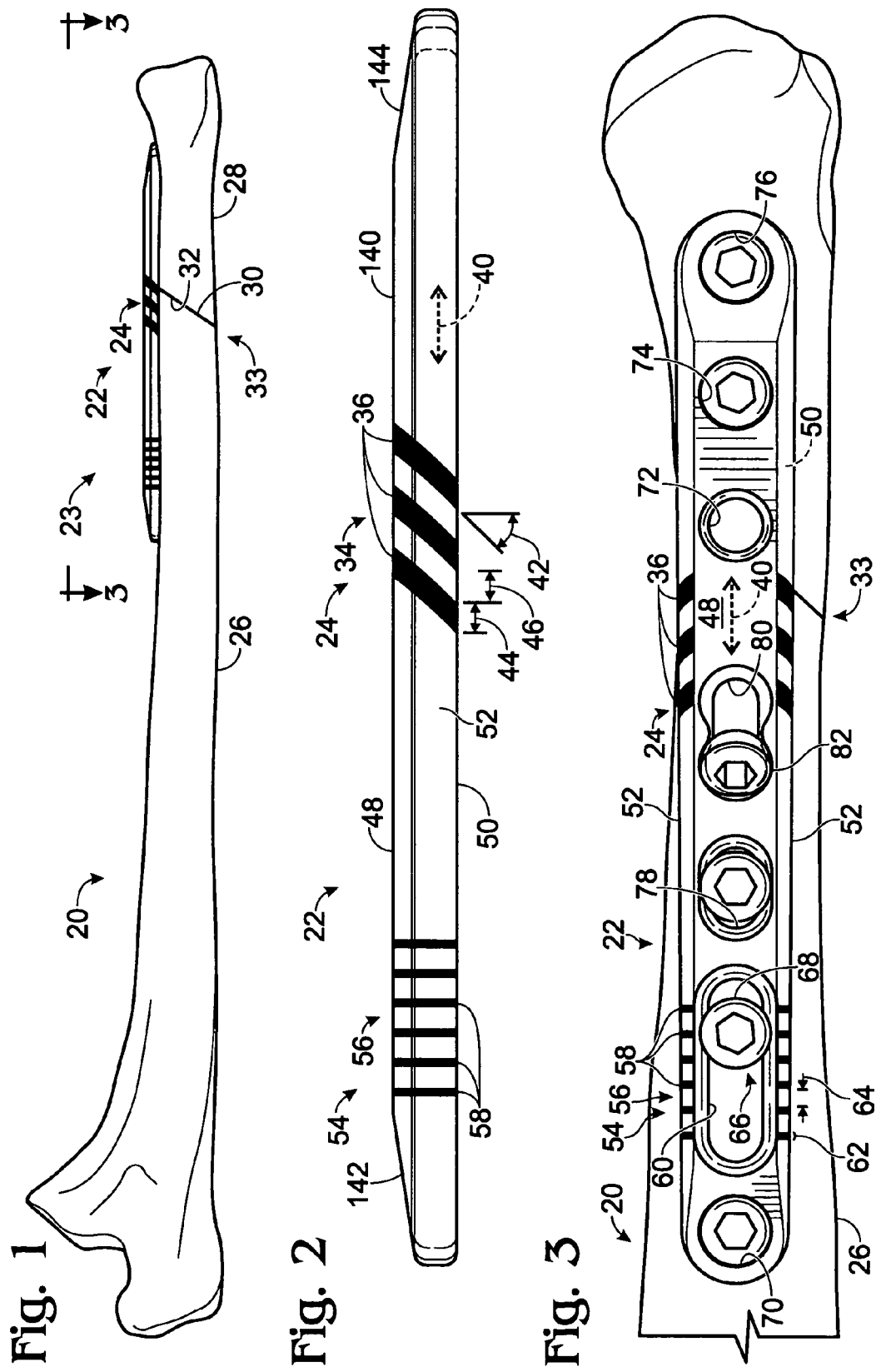

OSTEOTOMY SYSTEMS

CROSS-REFERENCES

The following U.S. patent applications are incorporated herein by reference: Ser. No. 10/716,719, filed Nov. 19, 2003; Ser. No. 10/717,015, filed Nov. 19, 2003; Ser. No. 10/717,399, filed Nov. 19, 2003; Ser. No. 10/717,401, filed Nov. 19, 2003; Ser. No. 10/717,402, filed Nov. 19, 2003; Ser. No. 10/731,173, filed Dec. 8, 2003; Ser. No. 10/873,522, filed Jun. 21, 2004; Ser. No. 10/968,850, filed Oct. 18, 2004; Ser. No. 11/071,050, filed Feb. 28, 2005; Ser. No. 11/109,985, filed Apr. 19, 2005; Ser. No. 11/112,858, filed Apr. 22, 2005; and Ser. No. 11/330,802, filed Jan. 11, 2006.

BACKGROUND

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that become damaged should be repaired promptly and properly. Typically, a cut or fractured bone is treated using a fixation device, which reinforces the bone and keeps it aligned during healing. Fixation devices may include external fixation devices (such as casts or fixators) and/or internal fixation devices (such as bone plates, nails (rods), and/or bone screws, among others).

Despite the use of fixation devices, bones may heal with a reduced length. For example, fractures of the radius bone in the forearm often result in radial shortening due to axial tension exerted by soft tissue as the fractures heal. Accordingly, the other forearm bone, the ulna, becomes longer relative to the radius. As a result, the distal ulna may impinge on the carpal bones of the wrist, causing inflammation and pain. A common treatment for this condition involves shortening the ulna through osteotomy to restore proper relative lengths of the ulna and radius.

In other cases, a bone may grow to an abnormal relative length that affects proper skeletal function. For example, due to a developmental defect, the ulna may be longer than normal such that the ulna impinges on the carpal bones.

Osteotomy systems for shortening bones have been disclosed by others. Generally, these systems involve a guide that physically directs a saw through a bone according to the position of the guide. However, these systems may suffer from various inadequacies, such as lack of flexibility and/or speed in guide positioning.

SUMMARY

The present teachings provide systems, including methods, apparatus, and kits, for performing osteotomies to cut bone and, optionally, to adjust bone length.

BRIEF DESCRIPTION OF THE DRAWINGS

FIG. 1 is a medial view of a shortened left ulna being fixed with a bone plate of an exemplary osteotomy system after the ulna was cut along a pair of spaced cutting paths selected according to a visual guide of the bone plate, in accordance with aspects of the present teachings.

FIG. 2 is a side view of the bone plate of FIG. 1 in the absence of bone.

FIG. 3 is an anterior view of the left ulna of FIG. 1 (and a top view of the bone plate), taken generally along line 3-3 of FIG. 1.

DETAILED DESCRIPTION

Figure 4:
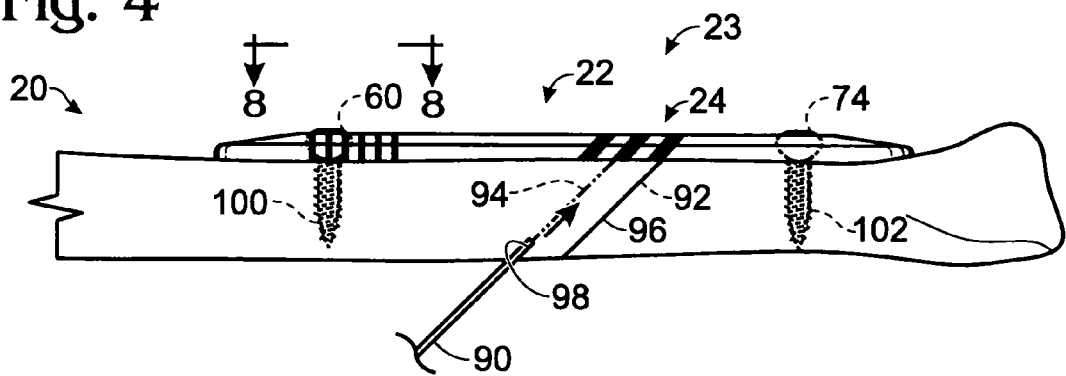
FIGS. 4-7 are a series of medial views of a distal portion of the left ulna of FIG. 1 and corresponding to configurations produced during use of the osteotomy system of FIG. 1 to shorten the left ulna.

The present teachings provide systems, including methods, apparatus, and kits, for performing osteotomies to cut bone and, optionally, to adjust bone length. The systems may include a guide(s) for a cutting tool (e.g., a saw) and a bone plate that includes and/or positions the guide and fixes the bone after the bone is cut.

The guide may be a visual guide and/or a mechanical guide. The visual guide may include an array of graduations disposed on the bone plate. The array of graduations may be visible from the side of the bone plate and/or from above the outer surface of the bone plate, when the bone plate is secured to bone. Accordingly, the array of graduations may offer a set of visible marks that facilitate orienting and/or axially positioning a cutting tool by eye, to, for example, excise a selected length of the bone for shortening the bone. The mechanical guide may be a component that connects to the bone plate, to physically guide a cutting tool. In some embodiments, the mechanical guide may be adjustable continuously over a range of positions.

The bone plate also or alternatively may include a set of graduations arrayed along an oblong aperture of the bone plate. The set of graduations may provide a gauge to facilitate measuring movement of a bone fragment (i.e., a cut or broken piece of bone, such as a segment of cut bone) relative the bone plate, using a bone fastener received in the oblong aperture as a reference index for the position of the bone fragment. The measured movement may enable a practitioner to determine how much the length of a cut (or fractured) bone has been changed as a result of axial compression or distraction of the cut (or fractured) bone.

Furthermore, the system may include a compression-distraction device. The compression-distraction device may be operated to urge bone segments together and/or apart via engagement, for example, with one or more bone fasteners extending through the bone plate and disposed in the bone segments.

Overall, the osteotomy systems of the present teachings may offer one or more advantages. For example, the systems may offer a simpler and/or more flexible approach to selecting cutting paths in bone, more efficient surgical procedures, and/or more accurate and/or controllable changes to bone length, among others.

Further aspects of the present teachings are described in the following sections, including (I) overview of an exemplary osteotomy system, (II) bone plates, (III) guides and gauges, (IV) compression-distraction devices, (V) osteotomy kits, (VI) methods of cutting bone and adjusting bone length, and (VII) examples.

I. OVERVIEW OF AN EXEMPLARY OSTEOTOMY SYSTEM

FIG. 1 shows a medial view of a shortened left ulna 20 being fixed with a bone plate 22 of an exemplary osteotomy system 23. Ulna 20 may be cut along a pair of spaced cutting paths selected according to a visual guide 24 of the bone plate, to delete a segment of the bone. Resulting bone segments 26, 28 of the ulna may be compressed axially, for example, to abut cut surface 30, 32 of the segments at a segment junction 33 and thus reduce the length of the ulna. Bone plate 22 then may be secured fixedly to both bone segments to fix the cut ulna, allowing the ulna to heal in a shortened condition.

FIG. 2 shows a magnified side view of bone plate 22 in the absence of bone, and FIG. 3 shows an anterior view of the ulna with the bone plate attached to the ulna. Visual guide 24 may include an array 34 of graduations or guide marks 36 disposed on the surface of the bone plate. Graduations 36 may have an angular disposition (e.g., an oblique disposition as shown here) relative to a long axis 40 of the bone plate. The angular disposition of graduations 36 thus may provide a reference angle 42 or orientation for orienting each cut in bone. The graduations also may have a width 44 and a spacing 46, which may be the same (as shown here) or may be different. In any case, the width and/or spacing may be predefined to form a guide that allows selection and/or measurement of the relative positions of spaced cuts in bone, such as by alignment with and/or reference to the guide.

Graduations 36 may be disposed on any suitable surface of the bone plate, such that the graduations are visible from any suitable position or in any suitable direction. For example, the graduations may be disposed on an outer face 48 (or on an inner face 50) of the bone plate, to provide graduations that are visible from a position normal to and outward of (or inward of) the outer face (or inner face). The graduations thus may be visible from positions directly above and/or directly below the bone plate, with the bone plate in the horizontal orientation of FIG. 2. Alternatively, or in addition, the graduations may be disposed on one or both opposing sides 52 of the bone plate, to provide visibility from positions directly lateral to the bone plate (from one or both sides of the bone plate) and in a direction generally parallel to the inner and outer faces. Here, graduations 36 are disposed on outer face 48 and on both opposing lateral sides 52. Graduations on both opposing sides may provide visibility from opposing sides of an ulna to which the bone plate is attached. Furthermore, graduations on both opposing sides, alternatively or in addition, may facilitate use of the bone plate on both the left and right ulna.

Bone plate 22 also may include a gauge 54 for measuring movement of the plate relative to bone and/or movement of bone fragments (or bones) relative to one another. Gauge 54 may include an array 56 of gauge marks or graduations 58 arranged axially on the plate relative to one another, such as along an oblong aperture 60 of the bone plate (see FIG. 3). Gauge marks 58 may have a predefined width 62 and/or spacing 64 that allows a visual determination of changes in the position of a reference site, such as a marked site 66 on, in, and/or adjacent bone. Here, a bone fastener (a bone screw) 68 has been received in oblong aperture 60 and extends into proximal segment 26 of the ulna. Accordingly, in this configuration, axial motion of the proximal segment relative to the bone plate would be reflected in axial motion of bone screw 68 along the oblong aperture. Gauge marks 58 may be disposed on one or both opposing sides 52 and/or on outer face 48 (and/or the inner face) of the bone plate.

The bone plate may have any suitable apertures for any suitable purposes, such as for receiving fasteners that secure the bone plate to bone and/or for attachment of a mechanical guide, among others. For example, bone plate 22 may include a plurality of circular apertures 70-76, a pair of oblong apertures 60 and 78 with an oval shape, and an oblique aperture 80 (see FIG. 3). The oblique aperture may be disposed adjacent visual guide 24 and may have a bore and/or a countersink oriented at an oblique angle, such that a fastener 82 placed into the oblique aperture may span the bone segments across segment junction 33. Here, the oblique aperture is elongate due to overlapping openings capable of receiving a fastener in alternative, opposing oblique orientations.

FIGS. 4-7 show a series of medial views of a distal portion of left ulna 20 before, during, and/or after shortening the ulna with osteotomy system 23. The configurations presented here thus illustrate an exemplary method of adjusting a bone length.

FIG. 4 shows ulna 20 as the ulna is being cut by a cutting tool, such as a saw 90, along cutting paths 92, 94 selected according to visual guide 24. Corresponding spaced cuts 96, 98 thus may be placed with reference to the visual guide, such as generally parallel to and/or aligned with the graduations of the visual guide. Prior to making any cuts, bone plate 22 may be secured to ulna 20 using bone screws 100, 102 received, for example, in oblong aperture 60 proximal to the visual guide and aperture 74 (and/or 72 and/or 76) distal to the visual guide (see FIG. 3 also).

Figure 5:
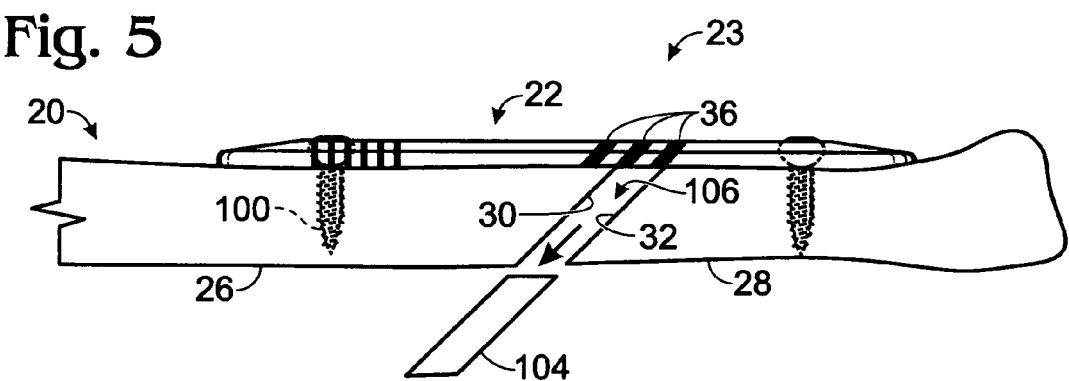

FIG. 5 shows ulna 20 after both cuts have been completed through the ulna. A segment 104 of the ulna may be released and segments 26, 28 with cut surfaces 30, 32, respectively, may be created. The cut surfaces may be spaced by a gap 106 about the same size as segment 104 (plus the size of kerfs, if any, created by cutting bone. Furthermore, segments 26, 28 may remain fixed relative to one another via the bone plate, which may act as a frame for positioning the segments.

In an exemplary embodiment, graduations 36 may have both a width and an edge-to-edge spacing of two millimeters. Accordingly, with this width, spacing, and the exemplary placement of cuts shown in FIG. 5, a deletion of six millimeters would be created in the ulna.

Figure 6:
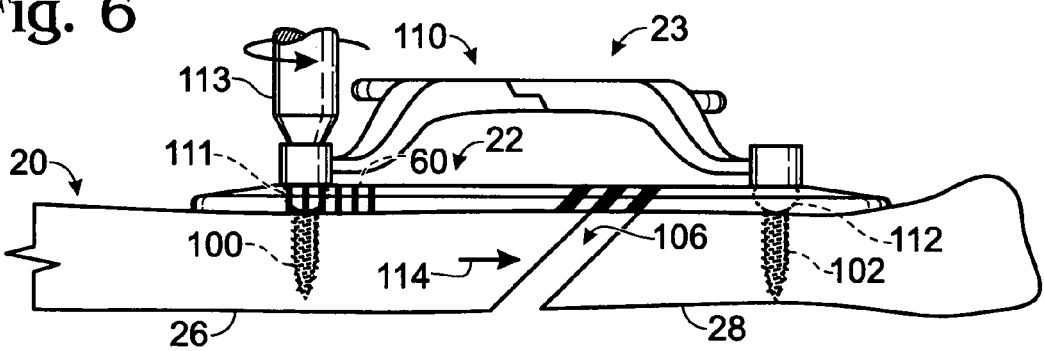

FIG. 6 shows ulna 20 ready to be compressed to close gap 106. A compression-distraction device 110 may be engaged with bone screws 100, 102 via respective heads 111, 112 of the bone screws. Proximal bone screw 100 may be loosened via a driver 113 to allow movement of the proximal bone screw (and its associated proximal bone segment) along oblong aperture 60. The compression-distraction device then may be operated to urge bone segments 26, 28 together axially, indicated at 114. In some embodiments, a distal bone screw also or alternatively may be disposed in an oblong aperture of the bone plate, to allow movement of the distal bone segment relative to the bone plate. (For example, bone plate 22 may be rotated 180 degrees on bone, relative to the orientation shown here, to switch the relative positions of its proximal and distal ends, and/or a bone plate with a different configuration of apertures may be used.)

Figure 7:
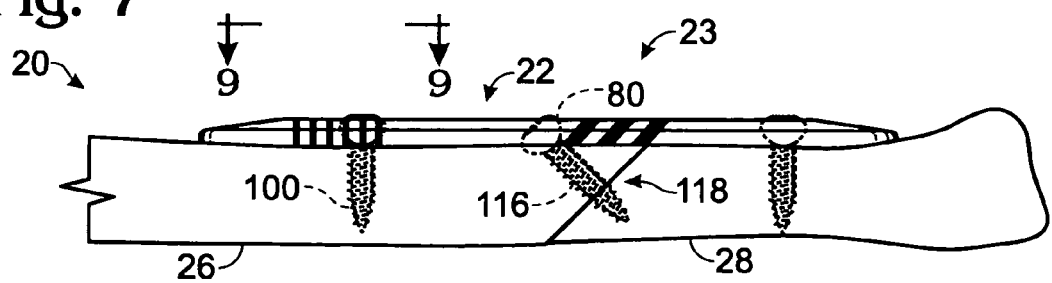

FIG. 7 shows ulna 20 in a shortened configuration after compression of its bone segments. After compression, the proximal bone screw may be tightened to fix the position of the proximal bone screw relative to the oblong aperture and thus fix the proximal bone segment relative to the bone plate. Furthermore, one or more additional fasteners may be installed through the bone plate into bone, to further stabilize the shorted configuration. For example, an oblique bone screw 116 may be placed at an angle through oblique aperture 80 (see FIG. 3 also) to span the bone segments, indicated at 118. Additional bone screws also may be installed through the plate and into bone, such as to achieve the configuration of bone screws of FIG. 3.

Figure 8:
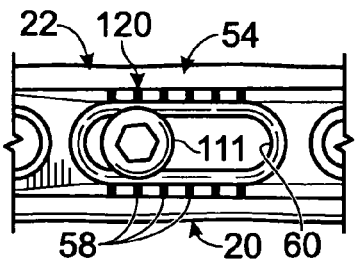
FIG. 8 is a fragmentary view of the left ulna and bone plate of FIG. 4, taken generally along line 8-8 of FIG. 4.
Figure 9:
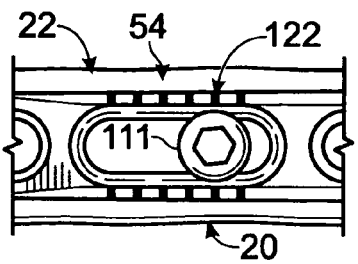
FIG. 9 is a fragmentary view of the left ulna and bone plate of FIG. 7, taken generally along line 9-9 of FIG. 7.

FIGS. 8 and 9 collectively show gauge 54 of bone plate 22 indicating a change in bone length produced by shortening ulna 20. Head 111 of the proximal bone screw may serve as an index for alignment with gauge marks 58. For example, FIG. 8 shows head 111 disposed toward the proximal end of oblong aperture 60, before the ulna is shortened, in alignment with a gauge mark (here, opposing gauge marks), indicated at 120. In some embodiments, the initial position of the bone screw within an oblong aperture may be aligned with the most proximal (or most distal) gauge mark, to provide the greatest potential range of motion of the bone screw upon compression (or distraction). However, the head may be aligned with an internal gauge mark at the outset, if desired, as shown here, particularly for a bone deletion of less than the length of the gauge.

FIG. 9 shows head 111 disposed in alignment with a more distal gauge mark, indicated at 122, after the ulna has been shortened. In an exemplary embodiment, gauge marks 58 may have a center-to-center spacing of two millimeters. Accordingly, with this exemplary spacing, the ulna is shortened here by six millimeters, which corresponds to the length of bone removed, as indicated by visual guide 24 (see FIG. 5 and corresponding description above).

II. BONE PLATES

Bone plates of the present teachings generally comprise any plate-like fixation device configured for attachment to bone. The bone plates generally have a low enough profile on bone that they can be used for internal fixation, that is, with the bone plates disposed mostly or completely under the skin of plate recipients. The bone plates may be of a sturdy yet malleable construction. Generally, the bone plates should be stiffer and stronger than the section of bone spanned by each plate, yet flexible (e.g., springy) enough not to strain the bone significantly. The bone plates may be configured to reduce irritation to the bone and surrounding tissue. For example, the bone plates may have a low and/or feathered profile to reduce their protrusion into overlying tissue and rounded, burr-free surfaces to reduce the effects of such protrusion. The bone plates may have any suitable shape, structure, apertures, and composition, as described further below.

A. Bone Plate Shape and Structure

The bone plates of the present teachings may have any shape suitable for use on their intended target bones. The bone plates may be shaped for use on any suitable bone or bones to be cut and/or fixed, including a bone of the arms (such as a humerus, a radius, and/or an ulna), a bone of the legs (such as a femur, a tibia, and/or a fibula), a bone of the hands (such as a carpal, metacarpal, and/or phalange), a bone of the feet (such as a tarsal, metatarsal, and/or phalange), a clavicle, a rib, a scapula, a pelvic bone, a vertebra, and/or the like. The bone may have any suitable condition to be treated, including a fracture, a malunion, a nonunion, a structural weakness, an undesirable length and/or angulation, and/or the like. The condition may affect any suitable portion of the bone, such as a diaphyseal (shaft) and/or a metaphyseal (end) region of the bone. In exemplary embodiments, the condition affects an ulna bone relative to an adjacent radius bone.

Each bone plate may be configured for use on any suitable side or sides of the body. For example, the bone plate may be configured for use on both the left side and right side of the body/skeleton, such as when the bone plate has bi-lateral mirror symmetry. Alternatively, each bone plate may be configured for use on either the left side or right side of the body/skeleton, but not both.

Each bone plate may be shaped and sized for use on any position of a target bone. For example, the bone plate may be shaped for use near an end of a bone, with a shank or body portion of the bone plate disposed more centrally on a shaft of the bone, and a widened head portion of the bone plate disposed more towards a metaphyseal region of the bone. Alternatively, the bone plate may lack a widened head portion, for example, if the bone plate is configured to be used more centrally on only a shaft of the bone.

Each bone plate may have any suitable contour. In some examples, the bone plate may be supplied in a pre-contoured configuration (e.g., by pre-operative bending, molding, and/or machining, among others) to include an inner surface that is complementary to a nonplanar surface region of a target bone. The bone plate thus may be pre-contoured according to an average or representative surface geometry of a target bone. Alternatively, or in addition, the bone plate may be contoured peri-operatively (e.g., by bending), to adjust its shape before and/or during its installation on bone, to improve, for example, the fit of the bone plate on a target bone for particular individuals and/or on different regions of the target bone.

The bone plate may have proximal and distal portions connected to one another through a bridge or junction region. The junction region may be joined unitarily to each of the proximal and distal portions, to provide a plate member of unitary construction, or may provide a site at which discrete proximal and distal plate components are connected to each other, to provide a plate member of non-unitary construction. The junction region may be configured to allow proximal and distal portions of each plate to slide, bend, turn, and/or twist relative to one another. Alternatively, or in addition, the junction region may provide a site at which a guide device, such as a mechanical cutting guide and/or a drill guide, may be attached to the bone plate. Fasteners also or alternatively may be placed into bone from the junction region.

Each bone plate may be generally elongate (at least before bending), with a length L, a width W, and a thickness T. Here, length L>width W>thickness T. In use, the long axis of the bone plate may be aligned with the long axis of its target bone and/or may extend obliquely and/or transversely relative to the long axis.

The thickness of the bone plate generally is defined by a distance between inner (bone-facing) and outer (bone-opposing) surfaces of the plate. The thickness may be generally constant, at least locally within the bone plate, such that the inner and outer surfaces of the bone plate are generally complementary. Alternatively, the inner and outer surface may have distinct topographies, for example, an inner surface that is concave and an outer surface that is a combination of convex and planar. However, the thickness of the plate may vary according to the intended use, for example, to make the bone plate thinner as it extends over protrusions (such as processes, condyles, tuberosities, and/or the like), reducing its profile and/or rigidity, among others. The thickness of the bone plate also may be varied to facilitate use, for example, to make the plate thinner, to facilitate bending where it typically needs to be contoured peri-operatively. In this way, the plate may be thicker and thus stronger in regions where the plate typically does not need to be contoured, for example, regions of the plate that are placed along the shaft of the bone, among others. In some examples, the proximal portion of each bone plate may be thicker than the distal portion and/or the bridge region disposed between the proximal and distal portions. A thinner bridge region may permit adjustment of the relative angular disposition of the proximal and distal portions by bending and/or twisting the plate at the bridge region. A thinner distal portion may reduce irritation by reducing the profile of this portion of the bone plate. In some examples, the proximal and distal portions may have about the same thickness, or the distal portion may be thicker than the proximal portion.

Each bone plate may be unitary or may include two or more discrete components. The two or more discrete components may be connected through a mechanical joint that enables translational and/or pivotal movement to adjust the shape and/or size of the bone plate. Further aspects of unitary and multi-component bone plates that are adjustable are described in the patent applications listed above under Cross-References, which are incorporated herein by reference, particularly U.S. patent application Ser. No. 10/716,719, filed Nov. 19, 2003; U.S. patent application Ser. No. 10/717,015, filed Nov. 19, 2003; U.S. patent application Ser. No. 717,399, filed Nov. 19, 2003; and U.S. patent application Ser. No. 10/717,402, filed Nov. 19, 2003.

B. Bone Plate Apertures

The bone plates generally include a plurality of apertures (openings) configured to perform similar or different functions. The apertures may be adapted to receive fasteners for affixing the bone plates to bone. The apertures also or alternatively may function to alter the local rigidity of the bone plates and/or to facilitate blood flow to a fracture or surgical site to promote healing, among others. In some examples, one or more apertures of a bone plate may be configured for coupling a guide device and/or a compression-distraction device to the bone plate. The aperture(s) for the guide device also may be used for placement of a fastener(s) into bone after the guide device has been removed, or the aperture(s) may be left unoccupied. Each aperture of a bone plate may have any suitable shape, including non-elongate (such as circular) or elongate (also termed oblong) (such as oval, elliptical, rectangular, etc.). Apertures may be created and/or tapped (threaded) pre-operatively, such as during the manufacture of the plates, and/or peri-operatively, such as with the plates disposed on bone. Further aspects of tapping apertures peri-operatively are described in U.S. patent application Ser. No. 10/873,522, filed Jun. 21, 2004, which is incorporated herein by reference.

Individual apertures may be locking or nonlocking. Exemplary locking apertures include a thread, ridge, and/or lip for engaging relatively complementary thread structure on a fastener, to restrict axial movement of the fastener into and out of the aperture. The thread and/or a wall of the aperture also may be configured to stop over-advancement of a fastener. For example, the thread may terminate in a dead end adjacent the inner surface of the plate, and/or the thread or aperture wall may taper toward the inner surface. Alternatively, or in addition, structure to stop over-advancement of the fastener may be included in the fastener. Other locking apertures are described in the patent applications listed above under Cross-References, which are incorporated herein by reference, particularly U.S. patent application Ser. No. 11/071,050, filed Feb. 28, 2005.

The bone plates may have one or more openings configured as slots. A slot, also termed an oblong opening, is any opening having a length that is greater than its width. The slot may be linear, arcuate, or angled, among others. The slot (or any other type of bone plate aperture) may include a countersink structure to receive a head of a bone screw. The countersink structure may be configured, as in a compression slot, to exert a force generally parallel to the long axis of the slot when a bone screw is advanced against the countersink structure. Slots may extend axially, that is, in general alignment with the long axis of the plate, or transversely, that is, substantially nonparallel to the long axis (oblique to the long axis or orthogonal to the long axis). Each bone plate may have one or more axial slots and one or more transverse slots. The slots may be used to adjust the translational and/or angular disposition of each bone plate on bone. Further aspects of slots that may be included in the bone plates of the present teachings are described further in the patent applications listed above under Cross-References, which are incorporated herein by reference, particularly, U.S. patent application Ser. No. 10/717, 015, filed Nov. 19, 2003.

The bone plates may be configured to receive wires. Each bone plate thus may include one or more holes (generally of smaller diameter) extending through the plate between inner and outer surfaces of the plate. Alternatively, or in addition, the bone plates may be configured to receive and retain wires that extend over (or under) the plates, rather than through the plates. Further aspects of bone plates configured to receive wires are described in the patent applications listed above under Cross-References, which are incorporated herein by reference, particularly U.S. patent application Ser. No. 11/109,985, filed Apr. 19, 2005.

C. Plate Materials

A bone plate of the present teachings may be substantially formed of, or may include, any suitable biocompatible material(s) and/or bioresorbable (bioabsorbable) material(s). Exemplary biocompatible materials that may be suitable for the bone plate include (1) metals/metal alloys (for example, titanium or titanium alloys, cobalt-chrome alloys, stainless steel, etc.); (2) plastics (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) ceramics (for example, alumina, beryllia, calcium phosphate, and/or zirconia, among others); (4) composites (for example, carbon-fiber composites); (5) bioresorbable materials or polymers (for example, polymers of $\alpha$-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-$\beta$-hydroxybutyrate, poly-$\beta$-hydroxypropionate, poly-$\delta$-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.); and/or the like. In some examples, one or more of these materials may form the body of a bone plate and/or a coating thereon.

Further aspects of bone plates that may be suitable for use in osteotomy systems of the present teachings are described in the patent applications listed above under Cross-References, which are incorporated herein by reference, particularly U.S. patent application Ser. No. 10/716,719, filed Nov.

19, 2003; U.S. patent application Ser. No. 10/717,015, filed Nov. 19, 2003; U.S. patent application Ser. No. 717,399, filed Nov. 19, 2003; U.S. patent application Ser. No. 10/717,402, filed Nov. 19, 2003; and U.S. patent application Ser. No. 10/731,173, filed Dec. 8, 2003.

III. GUIDES AND GAUGES

The osteotomy systems of the present teachings may include one or more guides and/or gauges. The guides may be suitable to facilitate selection of the angle and/or axial position of each cut in bone and/or to measure the spacing between cuts in bone. The guides may be visual guides that allow a practitioner to guide a cutting tool "by eye" based on one or more guide marks. Alternatively, or in addition, the guides may be mechanical guides that physically guide a cutting tool by restraining the motion of the cutting tool. The gauges may be integral to the guides and/or may be separate features of the osteotomy systems that facilitate linear and/or angular measurement.

A guide/gauge may include an array of graduations. A "graduation," as used herein is any mark that indicates a position, dimension, and/or orientation. The position/dimension/orientation may be predefined in relation to the bone plate (e.g., in relation to an end(s), a side, and/or a face(s) of the plate), one or more other graduations, another component of the osteotomy system, and/or bone, among others. The graduations may be, for example, line segments (straight and/or curved), dots, geometrical shapes (e.g., circles, polygons, etc.), alphanumeric characters (e.g., letters and/or numbers), and/or the like.

An array of graduations may have any suitable arrangement. The array may be linear or nonlinear (e.g., curved). The graduations may have a uniform spacing (i.e., the same spacing between each adjacent pair of graduations) or a nonuniform spacing (i.e., a different spacing between at least two pairs of adjacent graduations). In addition, the graduations may have the same width or at least two different widths (e.g., wide and narrow line segments). The spacing and width may be the same or may be different (e.g., the width may be substantially less than the spacing or vice versa). Furthermore, the spacing and/or width may correspond to any suitable unit of linear measurement (e.g., a unit provided by the metric system, such as about 1 to 5 millimeters, or about ½, 1, 2, 3, 4, and/or 5 millimeters, among others), including corresponding directly to a whole unit of linear measurement or an integer multiple thereof (e.g., a width/spacing of one, two, three or more millimeters. Alternatively, the width/spacing may be a fraction of a whole unit of linear measurement (e.g., ½, ¼ millimeters, among others). Any suitable region of a graduation may be used for measurement, such as the center, an edge (or opposing edges; see FIG. 5), or both, among others. Furthermore, the array may have any suitable number of graduations, such as two, three, four, or more. In some embodiments, a single graduation, rather than an array of graduations, may be suitable.

An array of graduations may have any suitable length. For example the array of graduations may be about one, two, or more centimeters (10, 20, or more millimeters) in length.

The graduations within an array may be the same type of mark (e.g., an array of dots) or different types of marks (e.g., an array of dots and dashes (line segments)). Accordingly, the graduations of an array may be distinguishable by position, by appearance, or both. In some embodiments, at least one position within the array may have two or more distinct, associated marks, such as a position marker and an identifier for the position marker (e.g., a line segment and a number or letter that identifies the line segment).

The graduations may have any suitable connection to a bone plate. In some examples, the graduations may be integral to the bone plate. Exemplary integral graduations may be formed by surface modifications or variations of the bone plate, such as via a surface topography (e.g., projections and/or depressions that are machined, molded, or added to the surface of the bone plate) and/or by a global, regional, or local surface coating (e.g., by a paint, dye, and/or the like). In some examples, the graduations may be distinct from the bone plate, such as graduations provided by a discrete cutting guide and/or gauge that connects to the bone plate.

The graduations may have any suitable disposition relative to the bone plate. If integral (or non-integral) to the bone plate, the graduations may be disposed on (or adjacent) one or both opposing sides, one or both opposing ends, and/or one or both opposing faces of the plate. The graduations may be arrayed parallel to the long axis of the bone and/or oblique or orthogonal to this long axis. The graduations may have any suitable disposition along the long axis of the bone plate and may extend along any suitable portion of the bone plate. For example, the graduations have an axial disposition that partially or completely overlaps one or more apertures (e.g., lateral to the aperture on one or both sides of the aperture) or may be arrayed at axial positions that are partially, mostly, or completely nonoverlapping with apertures. In addition, the graduations may be disposed toward an end of the bone plate and/or generally in a generally central axial portion of the bone plate. Furthermore, the graduations may be arrayed over about the entire length, more than about one-half, less than about one-half, or less than about one-fourth of the length of the bone plate.

Each graduation may extend with any suitable orientation relative to the bone plate. The graduation thus may extend transversely (e.g., orthogonally and/or obliquely) and/or parallel to the long axis of the plate. If extending obliquely, the graduation may extend at any suitable angle relative to the long axis, such as orthogonally, about thirty to sixty degrees, or about 45 degrees, among others. A non-orthogonal angle may be suitable to, for example, increase the surface area of the cut ends of abutted bone segments.

In some examples, the graduations may be disposed in at least two distinct arrays. The arrays may be overlapping or nonoverlapping axially. The arrays thus may be spaced from one another axially and/or transversely. The arrays may be distinct from one another based on position, appearance (e.g., width, spacing, number, and/or type of graduation within each array), or both.

An osteotomy system of the present teachings may include a mechanical guide with any suitable connection to a bone plate. The mechanical guide may be integral to the bone plate or may be a separate component that connects to the bone plate. If a separate component, the mechanical guide may connect to the bone plate via complementary mating structure, fasteners (e.g., threaded fasteners, pins, clips, etc.), and/or the like. Furthermore, the mechanical guide may connect to the bone plate at only one position or at a plurality of alternative positions relative to the bone plate. Accordingly, the mechanical guide may define distinct cutting paths for a cutting tool by coupling (and uncoupling) the guide at distinct positions of the bone plate or by movement of a portion of the mechanical guide while the guide remains coupled to the bone plate. In any case, the guide may be capable of defining a continuous range of cutting paths for a cutting tool or a limited number of discrete cutting paths. The mechanical guide may include or lack graduations that indicate the position of a guide portion of the mechanical guide.

IV. COMPRESSION-DISTRACTION DEVICES

The osteotomy systems of the present teachings may include a device for compression and/or distraction of bone segments and/or bones relative to one another.

The device may have any suitable connection or engagement with bone fasteners, the bone plate, and/or bone. In some embodiments, the device may engage bone fasteners to compress or distract bone segments (or bones) into which the bone fasteners are installed. The device may be otherwise unconnected to the bone plate or bone, or fasteners also may connect the device to the bone plate or bone, such as by extending through one or more openings of the device.

The device may operate via any suitable user motion. Exemplary motions may include direct manual adjustment and/or manual adjustment via a tool, such as a driver that couples a user's hand(s) to the device.

V. OSTEOTOMY KITS

The osteotomy systems of the present teachings may provide kits for cutting bones and/or adjusting the length of bones. The kits may include one or more bone plates, fasteners (such as bone screws, wires, pins, clamps, etc.) for securing the bone plate(s) to bone and/or to another kit component(s), a mechanical guide device, a drill(s), a saw or related cutting tool, one or more compression-distraction devices, instructions for use, and/or the like. These components may be as described elsewhere in the present teachings. Some or all of the components of each kit may be provided in a sterile condition, such as packaged in a sterile container.

VI. METHODS OF CUTTING BONE AND ADJUSTING BONE LENGTH

The osteotomy systems of the present teachings may provide methods of cutting bone and/or adjusting the length of a bone. The methods may include any subset or combination of the following steps, performed in any suitable order, and any suitable number of times: (1) select a bone to be cut, (2) select a bone plate for the bone, (3) secure the bone plate to the bone, (4) select one or more sites at which the bone is to be cut, (5) cut the bone at the selected sites, (6) compress or distract the bone to shorten or lengthen the bone, and (7) fix the bone. A method of cutting a bone may be performed, for example, with any suitable combination of steps (1) through (5), and a method of adjusting a bone's length may be performed, for example, with any suitable combination of steps (1) through (7). Further aspects of the steps are described below.

A bone may be selected. The bone may be selected for any suitable reason, such for being relatively or absolutely too long or too short, having a malunion or a fracture, exhibiting the consequences of a developmental defect (e.g., a length and/or shape defect), etc. The bone may be a long bone or another bone of the skeleton. In some examples, the bone may be a forearm bone, such as an ulna or radius. In exemplary embodiments, the bone is an ulna (or radius) that does not correspond in length to an adjacent radius (or ulna) bone, such as due to a length deficiency (or excess) of the radius (or ulna) bone caused by an injury or developmental defect. Selecting a bone to be cut and/or adjusted in length also may include measuring the initial length of the bone, such as by radiography, visual inspection, mechanical testing, and/or the like, to determine whether or not the bone should be cut or adjusted in length. Furthermore, selecting a bone may include creating an incision through soft tissue on the anterior, posterior, lateral, and/or medial side of a limb, and in a proximal, distal, and/or central region of the limb, to access the bone. These and other suitable steps of the methods may be performed under sterile conditions and/or in a sterile field, for example, during surgery in an operating room.

A bone plate for the bone may be selected. The bone plate may have any of the features described elsewhere in the present teachings, such as a visual cutting guide, a gauge for measuring changes in bone length, an attachment site for a mechanical cutting guide, etc. The bone plate may be selected according to the bone to be cut and/or adjusted in length and thus may have a size and shape corresponding to the bone. For example, the bone plate may be contoured so that its inner surface is nonplanar and is complementary to a nonplanar, exterior surface region of the bone (such as a forearm bone). In some examples, the bone plate may be pre-contoured (e.g., by bending, machining, and/or casting, among others) according to an average anatomy of a bone within a population. The bone plate may be configured for use on both sides of the skeleton, or may be configured for use on a right bone or a left bone, but not both. In some examples, the bone plate may include indicia (e.g., one or more alphanumeric characters, one or more words, a color, a bar code, etc.) to identify the bone plate, the bone for which the bone plate is configured, the size of the bone plate, the handedness of the bone plate, the attributes of any associated gauge (e.g., spacings between graduations), and/or the like.

The bone plate may be secured to the bone. The bone plate may be disposed on any suitable surface along and/or around the bone, such as on a distal surface of an ulna bone, among others. The bone plate may be disposed such that the bone plate spans a site(s) at which the bone is to be cut. The bone plate may be secured by placement of fasteners through openings of the bone plate. The fasteners may include wires and/or bone screws, among others. The fasteners may be placed through bone plate openings disposed on opposing sides (or only one side) of a prospective cutting site(s) in the bone. In some examples, an oblong aperture(s) of the bone plate may be used to receive a fastener(s) that secures the bone plate to one (or both) side(s) of the prospective cutting site(s). Placement of fasteners may be facilitated with a guide device that directs placement of a wire, a drill, and/or a bone screw, among others.

One or more prospective cutting sites may be selected. For example, one cutting site may be selected to allow distraction of a cut bone, and two or more cutting sites may be selected to allow compression of the cut bone. Selection of the spacing between cutting sites may be based on the length of bone to be excised (e.g., based on pre-operative and/or peri-operative measurements). In some examples, the cutting sites may be selected according to a visual guide of the bone plate. The cutting sites thus may be oriented and axially disposed relative to the bone according to graduations of the visual guide that are selected to guide cutting. Alternatively, the cutting sites may be selected with a mechanical guide. Selection of cutting sites thus may include positioning the mechanical guide to define the cutting sites. Positioning may involve operation of a drive mechanism, manually sliding the mechanical guide along the bone plate (without uncoupling), and/or mounting the mechanical guide at each of two alternative positions along the bone plate, among others.

The bone may be cut at the selected sites. Cutting may be performed with a manually driven or power-driven cutting tool (e.g., a saw). Furthermore, cutting may performed by approaching the bone with the cutting tool from any suitable direction, such as opposing the bone plate and/or lateral to the bone plate (from a direction generally parallel to the inner and outer faces of the bone plate). The bone may be cut after all of the cutting sites have been selected or cutting may alternate with selection of the cutting sites. Furthermore, one or more additional cutting sites may be selected and additional cutting performed based on the outcome of earlier cutting operations. For example, a larger deletion of a bone may be created with an additional cut if an initial deletion is not sufficient to provide a desired shortening of the bone. The size of the deletion may be measured visually by comparing deletion endpoints with graduations of a visual guide, by observing a scale of a mechanical guide, by radiography, with a caliper, and/or the like.

The bone may be compressed or distracted, to respectively shorten or lengthen the bone. Compression or distraction may be performed with a compression-distraction tool. The tool may be coupled to the bone plate and/or bone, such as via fasteners, or may engage bone fasteners without attachment otherwise to the bone plate or bone. In any case, one or more bone fasteners may be adjusted or removed to allow the tool to perform compression or distraction and/or to fix a compressed or distracted configuration that is achieved with the tool. The direction and/or extent of compression or distraction by the tool may be controlled, for example, by operation of a worm/screw drive or a ratchet and pawl of the tool, manually engaging and urging portions of the tool together or apart, and/or the like. Furthermore, the extent of compression or distraction may be measured and/or monitored via a gauge. The gauge may be included in the tool, the bone plate, and/or may be a separate component.

The bone may be fixed such that the bone is stabilized in a shortened or lengthened condition. Fixation may include adjusting a bone fastener that is already installed and/or installation of one or more additional bone fasteners. Adjustment of a bone fastener may be performed with a compression-distraction tool holding the bone in a compressed or distracted configuration, or after disengagement/uncoupling of the tool.

The bone plate may be secured permanently or temporarily. In some examples, the bone plate may be left in place indefinitely. In some examples, the bone plate may be removed at a suitable time, such as after sufficient healing has occurred.

VII. EXAMPLES

The following examples describe selected aspects of exemplary osteotomy systems, particularly a bone plate, a mechanical guide, and a compression-distraction device for the systems. These examples are included for illustration and are not intended to limit or define the entire scope of the present teachings.

Example 1

Exemplary Bone Plate

This example describes selected aspects of an exemplary bone plate 22 for use in the osteotomy systems of the present teachings; see FIGS. 2 and 3. Additional aspects of the bone plate are described above, for example, in Section I.

Bone plate 22 may have any suitable geometry. The bone plate may be generally linear and may have a planar outer surface region 140 (see FIG. 2). The outer surface region may extend to beveled regions 142, 144 disposed adjacent opposing ends of the plate.

The bone plate may be shaped to fit onto a forearm bone, that is, the ulna and/or the radius. Accordingly, the bone plate may have an inner surface that is generally complementary to a surface region(s) of the forearm bone(s).

One or more of the plate's apertures may be locking apertures with a thread engagement structure, such as an internal thread. For example, aperture 72 may include an internal thread that allows this aperture to be used for mounting a mechanical guide, as described further in Example 2.

Example 2

Exemplary Osteotomy System with Mechanical Guide

Figure 10:
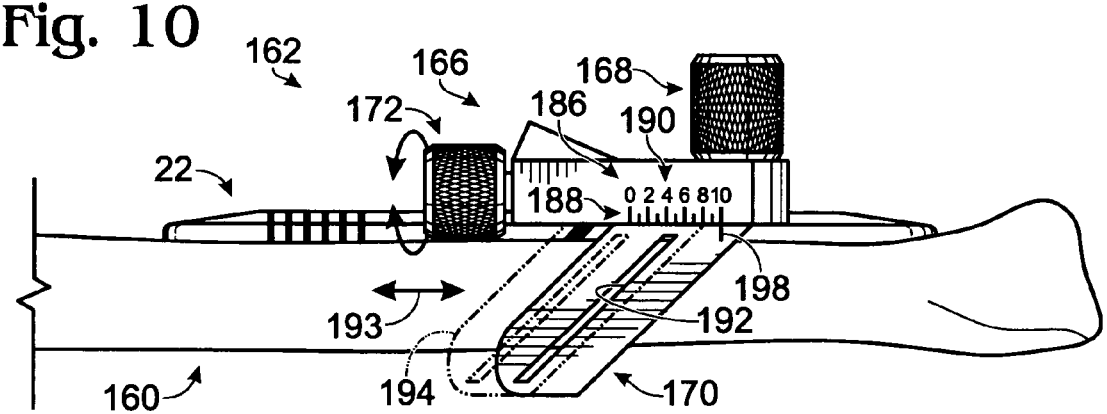
FIG. 10 is a medial view of a distal portion of a left ulna with selected portions of another exemplary osteotomy system attached to the ulna prior to cutting the ulna along a pair of spaced cutting paths selected via a mechanical guide of the osteotomy system, in accordance with aspects of the present teachings.
Figure 11:
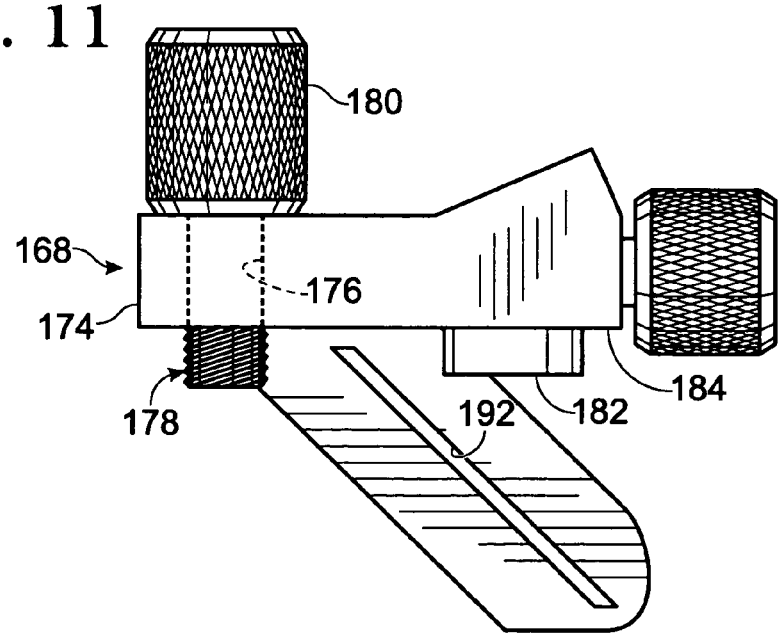
FIG. 11 is a view of the mechanical guide of FIG. 10 taken from the opposing side of the mechanical guide.
Figure 12:
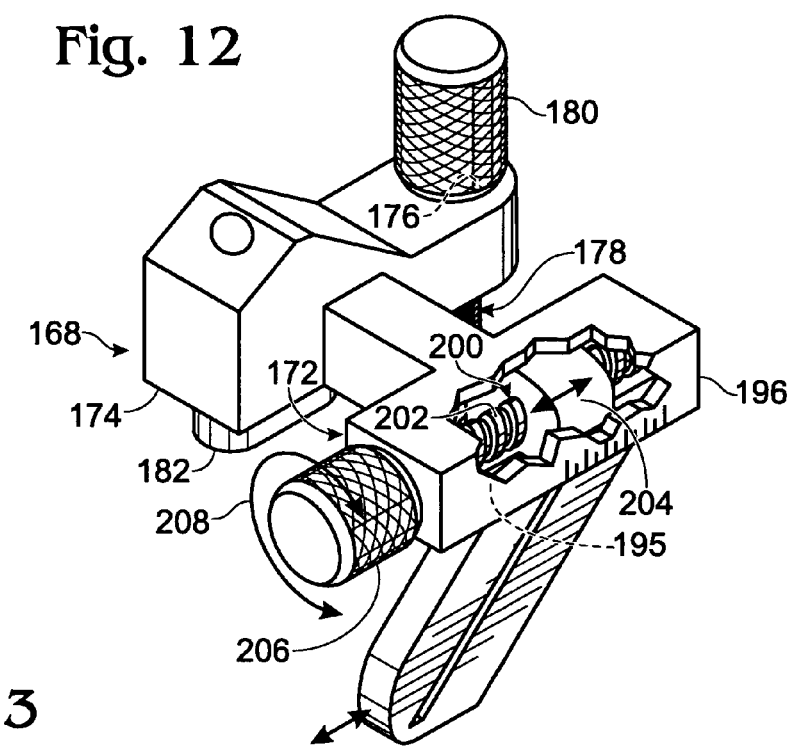
FIG. 12 is a broken view of the mechanical guide of FIG. 10, taken generally from above the mechanical guide, with a portion of the guide's housing broken away to reveal selected aspects of a manual drive mechanism of the guide.

This example describes an exemplary osteotomy system including a mechanical guide; see FIGS. 10-12.

FIG. 10 shows a distal portion of a left ulna 160 with selected portions of another exemplary osteotomy system 162 attached to the ulna. The system may include bone plate 22 (see FIGS. 1-3) to which a mechanical cutting guide 166 may be attached. Alternatively, the mechanical cutting guide may be attached directly to bone and/or to any other suitable bone plate, such as a bone plate lacking a visual guide for cutting. The mechanical cutting guide may be attached to the bone plate (and/or bone) before or after the bone plate is secured to bone. Mechanical guide 166 may have a mounting portion 168, a guide portion 170, and a drive mechanism 172 that adjustably positions the guide portion relative to the mounting portion.

Mounting portion 168 may include a frame 174 that is mounted fixedly on the bone plate (see FIGS. 11 and 12). The frame may define at least one opening 176 that receives a threaded fastener 178. The threaded fastener may extend through opening 176 for threaded engagement with a locking aperture of the bone plate (such as aperture 72; see FIG. 3). The threaded fastener may include a head 180 with tool engagement structure and/or that is enlarged (and, optionally, textured), as in the present illustration, to provide a handle portion for manual engagement. The frame may be fixed further by a protuberance or boss 182 that extends from an inner surface 184 of the frame (see FIG. 11). The protuberance may be sized to fit closely into elongate oblique aperture 80 of the bone plate (see FIG. 3). The frame also may provide a scale 186 including graduations 188 and/or numbers 190 (see FIG. 10). In exemplary embodiments, the numbers may represent millimeters and the scale may be about ten millimeters in length.

Guide portion 170 may provide a track or slot 192, for guiding a saw blade physically through bone (see FIGS. 10 and 11). The slot may be sized to receive the saw blade and also may restrict lateral movement of the blade by contact with guide walls flanking the slot. The slot may be disposed at any suitable angle for performing osteotomies, such as about 45 degrees, as shown here. In addition, the guide portion may be offset laterally (to the side) from the bone plate (see FIG. 10), such that the slot extends adjacent the bone, generally between opposing sides of the bone.

Guide portion 170 may be coupled in a fixed or movable configuration to the frame of the mechanical guide. If movable, the guide portion may be movable translationally along the bone plate (and bone), indicated by a double-headed arrow at 193 and by a guide portion in phantom outline at 194 (see FIG. 10). For example, the guide portion may move along a track 195 formed in a lateral housing 196 of frame 174 (see FIG. 12). The guide portion also may include an index 198 apposed to scale 186, to measure positional changes of the guide portion (see FIG. 10). In alternative embodiments, the guide portion may provide the scale and the frame may provide the index.

Drive mechanism 172 may be operable manually to change the longitudinal position of the guide portion along the plate and bone (see FIG. 12). The drive mechanism may include a screw drive 200 with a threaded shaft 202 and a complementary internally threaded carriage 204. The carriage may be attached to the guide portion and disposed in track 195. The threaded shaft may be coupled to the track via a pin that engages an annular groove of the threaded shaft, such that the threaded shaft is pivotable but otherwise held in position in the track. The threaded shaft thus may be disposed in threaded engagement with the carriage, such that rotation of the shaft moves the carriage and guide portion along the track. The threaded shaft may extend to form a head 206, which may be enlarged (and, optionally, textured) to provide a handle portion for manual operation of the drive mechanism by rotation, indicated at 208, of the handle portion. To delete a segment of bone, the guide portion may be moved to a suitable pair of measured longitudinal positions by operation of the drive mechanism and observation of the index relative to the scale, to guide a saw blade through the bone at each of these positions.

Example 3

Exemplary Compression-Distraction Device

Figure 13:
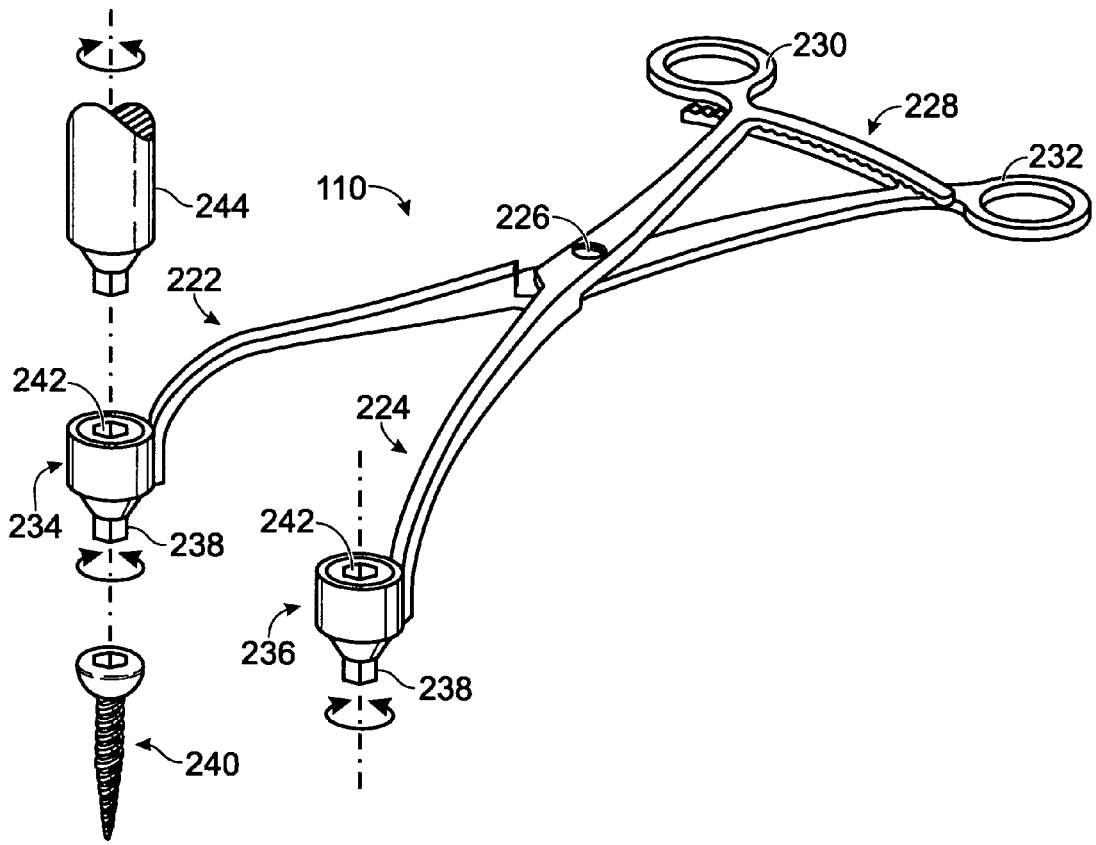
FIG. 13 is a view of an exemplary compression-distraction device that may be used in the osteotomy systems of the present teachings, with a pivotable coupler of the compression-distraction device aligned with a driver and a bone screw.

This example describes an exemplary compression-distraction device that may be included in or used with the osteotomy systems of the present teachings; see FIG. 13.

FIG. 13 shows a compression-distraction tool 110 for compressing (or distracting) cut bone by engagement of bone screws. The tool may be designed generally as a modified hemostat and was introduced in Section I above in relation to FIG. 6. The tool may include a pair of arm members 222, 224 coupled via a hinge joint 226 and held at a various angular positions, via a detent mechanism 228.

Each arm member may have any suitable structure. For example, the arm members may include handle regions 230, 232, such as finger grips, disposed proximally for manual manipulation of the arm members. In addition, the arm members may extend distally to pivotable couplers 234, 236. Each coupler may be structured to mate with the head of a bone screw that secures a bone plate to bone, generally on opposing sides of the region of bone that is cut (see FIG. 6). Accordingly, the coupler may include a fastener engagement structure (a projection or socket), such as hexagonal tip 238 shaped to mate with the head of a bone screw 240. One or both couplers 234, 236 may be pivotably connected to the arm members, for pivotal movement about a central axis of each coupler. Furthermore, one or both couplers may define a driver engagement structure, such as a socket 242, disposed opposite the fastener engagement structure. The driver engagement structure thus may receive a driver 244 that turns bone screws engaged by the couplers, for example, with the bone screws securing the bone plate to bone. Furthermore, relative pivotal movement of the arms members may change the separation between couplers 234, 236, to provide compression or distraction of bone fasteners and their attached bone segments.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

I claim:

1. A method of treating a bone condition, comprising:
coupling a bone plate to a bone, the bone plate including an outer face and opposing lateral sides each contiguous with the outer face, the bone plate also including an array of graduations each disposed on a lateral side and extending oblique to the bone plate on an outer surface region of the lateral side to define a plurality of oblique paths extending from the graduations, a maximum width of the bone plate at the array of graduations being less than a width of the bone where the bone plate is coupled to the bone;
cutting the bone along one or more of the oblique paths to form a pair of bone pieces; and
fixing the pair of bone pieces relative to one another with the bone plate.

2. The method of claim 1, wherein the steps of coupling and cutting are performed on a forearm bone.

3. The method of claim 2, wherein the steps of coupling and cutting are performed on an ulna.

4. The method of claim 1, further comprising a step of shortening the bone to a shorter form by axial compression of the bone after the step of cutting, wherein the step of fixing fixes the bone in the shorter form using the bone plate attached to the pair of bone pieces with a plurality of fasteners.

5. The method of claim 4, wherein the step of shortening includes a step of urging the pieces of the bone together via engagement of bone screws extending into the bone from the bone plate.

6. The method of claim 1, wherein the step of coupling includes a step of coupling a bone plate to a bone that is only one piece.

7. The method of claim 1, wherein the step of coupling disposes the array of graduations such that at least a portion of each graduation is visible from a position directly lateral to the bone plate.

8. The method of claim 1, wherein the step of cutting the bone includes a step of cutting completely through the bone at least twice to remove a segment of the bone.

9. The method of claim 1, further comprising a step of adjusting a length of the bone after the step of cutting by changing a position of at least one of the bone pieces with respect to the other bone piece, wherein the step of adjusting is performed before the step of fixing.

10. The method of claim 1, wherein the step of coupling is performed on a bone of a recipient, further comprising a step of disposing the bone plate at least mostly under the skin of the recipient.

11. The method of claim 1, wherein each graduation extends to a position on the outer face of the bone plate.

12. A method of treating a bone condition, comprising:
coupling a bone plate to a bone, the bone plate including an outer face and opposing lateral sides each contiguous with the outer face, the bone plate having an array of three or more uniformly-spaced graduations disposed on an outer surface region of the lateral side;
cutting the bone in alignment with one or more of the graduations to form a pair of bone pieces;
fixing the pair of bone pieces relative to one another with the bone plate; and
leaving the bone plate on the bone while the bone heals.

13. The method of claim 12, wherein the array of graduations is a first array, wherein the step of coupling is performed at least in part with a bone screw received in a slot of the bone plate, and wherein the bone plate has a second array of three or more uniformly-spaced graduations disposed along the slot and spaced axially from the first array.

14. The method of claim 13, further comprising a step of observing a change in position of the bone screw relative to the second array of graduations as the bone is compressed or distracted, to measure a change in overall bone length.

15. A method of treating a bone condition, comprising:
coupling a bone plate to a bone, at least in part with a bone screw received in a slot of the bone plate, the bone plate including a first array of graduations and a distinct second array of three or more uniformly-spaced graduations;
cutting the bone in alignment with one or more graduations of the first array of graduations, to form a pair of bone pieces; and
measuring a change in length of the bone resulting from compression or distraction of the bone, by observing a change in position of the bone screw with respect to the second array of graduations.

16. The method of claim 15, wherein the step of cutting includes a step of cutting the bone obliquely to a long axis of the bone.

17. The method of claim 15, wherein the first array includes three or more graduations that are uniformly spaced.

18. The method of claim 15, wherein each graduation of the first array extends oblique to the bone plate on an outer surface region of the bone plate.

* * * * *